(12) United States Patent
Elliott et al.

(10) Patent No.: US 8,425,550 B2
(45) Date of Patent: Apr. 23, 2013

(54) EMBOLIC COILS

(75) Inventors: Christopher J. Elliott, Hopkinton, MA (US); Patrick G. O'Connor, Mallow (IR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1466 days.

(21) Appl. No.: 11/000,741

(22) Filed: Dec. 1, 2004

(65) Prior Publication Data

US 2006/0116711 A1 Jun. 1, 2006

(51) Int. Cl.
*A61M 29/00* (2006.01)

(52) U.S. Cl.
USPC .......................................................... 606/200

(58) Field of Classification Search .................. 606/200; 623/1.22, 1.3, 1.31
See application file for complete search history.

(56) References Cited

U.S. PATENT DOCUMENTS

| | | | |
|---|---|---|---|
| 2,609,347 A | 9/1952 | Wilson | |
| 3,663,470 A | 5/1972 | Nishimura et al. | |
| 3,737,398 A | 6/1973 | Yamaguchi | |
| 3,921,632 A | 11/1975 | Bardani | |
| 3,957,933 A | 5/1976 | Egli et al. | |
| 4,025,686 A | 5/1977 | Zion | |
| 4,034,759 A | 7/1977 | Haerr | |
| 4,055,377 A | 10/1977 | Erickson et al. | |
| 4,076,640 A | 2/1978 | Forgensi et al. | |
| 4,094,848 A | 6/1978 | Naito | |
| 4,096,230 A | 6/1978 | Haerr | |
| 4,098,728 A | 7/1978 | Rosenblatt | |
| 4,110,529 A | 8/1978 | Stoy | |
| 4,159,719 A | 7/1979 | Haerr | |
| 4,191,672 A | 3/1980 | Salome et al. | |
| 4,198,318 A | 4/1980 | Stowell et al. | |
| 4,243,794 A | 1/1981 | White et al. | |
| 4,246,208 A | 1/1981 | Dundas | |
| 4,266,030 A | 5/1981 | Tschang et al. | |
| 4,268,495 A | 5/1981 | Muxfeldt et al. | |
| 4,271,281 A | 6/1981 | Kelley et al. | |
| 4,402,319 A | 9/1983 | Handa et al. | |
| 4,413,070 A | 11/1983 | Rembaum | |
| 4,427,794 A | 1/1984 | Lange et al. | |
| 4,428,869 A | 1/1984 | Munteanu et al. | |
| 4,429,062 A | 1/1984 | Pasztor et al. | |
| 4,442,843 A | 4/1984 | Rasor et al. | |
| 4,444,961 A | 4/1984 | Timm | |
| 4,452,773 A | 6/1984 | Molday | |
| 4,456,693 A | 6/1984 | Welsh | |
| 4,459,145 A | 7/1984 | Elsholz | |
| 4,472,552 A | 9/1984 | Blouin | |

(Continued)

FOREIGN PATENT DOCUMENTS

AU A-76186/98 10/1998
DE 233 303 2/1986

(Continued)

OTHER PUBLICATIONS

U.S. Appl. No. 10/927,868, filed Aug. 27, 2004, Richard et al.

(Continued)

*Primary Examiner* — Melanie Tyson
(74) *Attorney, Agent, or Firm* — Bingham McCutchen LLP

(57) ABSTRACT

Embolic coils, as well as related methods, devices, and compositions, are disclosed.

31 Claims, 7 Drawing Sheets

U.S. PATENT DOCUMENTS

| | | |
|---|---|---|
| 4,477,255 A | 10/1984 | Pasztor et al. |
| 4,492,720 A | 1/1985 | Mosier |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,708,718 A | 11/1987 | Daniels |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,900,303 A | 2/1990 | Lemelson |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,994,069 A | 2/1991 | Ritchart et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,021,059 A | 6/1991 | Kensey et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,108,407 A | 4/1992 | Geremia et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,167,624 A | 12/1992 | Butler et al. |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,226,911 A | 7/1993 | Chee et al. |
| 5,234,437 A | 8/1993 | Sepetka |
| 5,250,071 A | 10/1993 | Palermo |
| 5,253,991 A | 10/1993 | Yokota et al. |
| 5,256,146 A | 10/1993 | Ensminger et al. |
| 5,260,002 A | 11/1993 | Wang |
| 5,261,916 A | 11/1993 | Engelson |
| 5,262,176 A | 11/1993 | Palmacci et al. |
| 5,263,964 A | 11/1993 | Purdy |
| 5,263,992 A | 11/1993 | Guire |
| 5,288,763 A | 2/1994 | Li et al. |
| 5,290,310 A | 3/1994 | Makower et al. |
| 5,292,332 A | 3/1994 | Lee |
| 5,292,814 A | 3/1994 | Bayer et al. |
| 5,302,369 A | 4/1994 | Day et al. |
| 5,304,195 A | 4/1994 | Twyford, Jr. et al. |
| 5,312,415 A | 5/1994 | Palermo |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,324,306 A | 6/1994 | Makower et al. |
| 5,328,936 A | 7/1994 | Leifholtz et al. |
| 5,334,216 A | 8/1994 | Vidal et al. |
| 5,336,263 A | 8/1994 | Ersek et al. |
| 5,342,394 A | 8/1994 | Matsuno et al. |
| 5,344,452 A | 9/1994 | Lemperle |
| 5,344,867 A | 9/1994 | Morgan et al. |
| 5,350,397 A | 9/1994 | Palermo et al. |
| 5,354,290 A | 10/1994 | Gross |
| 5,354,295 A | 10/1994 | Guglielmi et al. |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,411,520 A | 5/1995 | Nash et al. |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,540,680 A | 7/1996 | Guglielmi et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,277 A * | 6/1997 | Mariant et al. ............... 606/191 |
| 5,639,710 A | 6/1997 | Lo et al. |
| 5,648,095 A | 7/1997 | Illum et al. |
| 5,648,100 A | 7/1997 | Boschetti et al. |

| | | | | | |
|---|---|---|---|---|---|
| 5,650,116 A | 7/1997 | Thompson | 6,090,925 A | 7/2000 | Woiszwillo et al. |
| 5,651,990 A | 7/1997 | Takada et al. | 6,096,344 A | 8/2000 | Liu et al. |
| 5,653,922 A | 8/1997 | Li et al. | 6,099,546 A | 8/2000 | Gia |
| 5,657,756 A | 8/1997 | Vrba | 6,099,864 A | 8/2000 | Morrison et al. |
| 5,681,576 A | 10/1997 | Henry | 6,100,306 A | 8/2000 | Li et al. |
| 5,695,480 A | 12/1997 | Evans et al. | 6,117,157 A * | 9/2000 | Tekulve .................... 606/200 |
| 5,695,740 A | 12/1997 | Porter | 6,139,963 A | 10/2000 | Fujii et al. |
| 5,698,271 A | 12/1997 | Liberti et al. | 6,149,623 A | 11/2000 | Reynolds |
| 5,701,899 A | 12/1997 | Porter | 6,159,206 A | 12/2000 | Ogawa |
| 5,715,824 A | 2/1998 | Unger et al. | 6,160,084 A | 12/2000 | Langer et al. |
| 5,716,981 A | 2/1998 | Hunter et al. | 6,162,377 A | 12/2000 | Ghosh et al. |
| 5,718,884 A | 2/1998 | Klaveness et al. | 6,165,193 A | 12/2000 | Greene, Jr. et al. |
| 5,723,269 A | 3/1998 | Akagi et al. | 6,179,817 B1 | 1/2001 | Zhong |
| 5,725,534 A | 3/1998 | Rasmussen | 6,190,373 B1 | 2/2001 | Palermo et al. |
| 5,733,925 A | 3/1998 | Kunz et al. | 6,191,193 B1 | 2/2001 | Lee et al. |
| 5,741,331 A | 4/1998 | Pinchuk | RE37,117 E | 3/2001 | Palermo |
| 5,746,734 A | 5/1998 | Dormandy, Jr. et al. | 6,214,331 B1 | 4/2001 | Vanderhoff et al. |
| 5,749,891 A * | 5/1998 | Ken et al. .................... 606/200 | 6,224,630 B1 | 5/2001 | Bao et al. |
| 5,752,974 A | 5/1998 | Rhee et al. | 6,224,794 B1 | 5/2001 | Amsden et al. |
| 5,760,097 A | 6/1998 | Li et al. | 6,231,586 B1 | 5/2001 | Mariant |
| 5,766,147 A | 6/1998 | Sancoff et al. | 6,235,224 B1 | 5/2001 | Mathiowitz et al. |
| 5,770,222 A | 6/1998 | Unger et al. | 6,238,403 B1 | 5/2001 | Greene, Jr. et al. |
| 5,779,668 A | 7/1998 | Grabenkort | 6,245,090 B1 | 6/2001 | Gilson et al. |
| 5,785,642 A | 7/1998 | Wallace et al. | 6,258,338 B1 | 7/2001 | Gray |
| 5,785,682 A | 7/1998 | Grabenkort | 6,261,585 B1 | 7/2001 | Sefton et al. |
| 5,792,478 A | 8/1998 | Lawin et al. | 6,264,861 B1 | 7/2001 | Tavernier et al. |
| 5,795,562 A | 8/1998 | Klaveness et al. | 6,267,154 B1 | 7/2001 | Felicelli et al. |
| 5,797,953 A | 8/1998 | Tekulve | 6,268,053 B1 | 7/2001 | Woiszwillo et al. |
| 5,800,453 A | 9/1998 | Gia | 6,277,392 B1 | 8/2001 | Klein |
| 5,800,454 A * | 9/1998 | Jacobsen et al. ............... 606/191 | 6,280,457 B1 | 8/2001 | Wallace et al. |
| 5,800,455 A | 9/1998 | Palermo et al. | 6,291,605 B1 | 9/2001 | Freeman et al. |
| 5,807,323 A | 9/1998 | Kriesel et al. | 6,296,604 B1 | 10/2001 | Garibaldi et al. |
| 5,813,411 A | 9/1998 | Van Bladel et al. | 6,296,622 B1 | 10/2001 | Kurz et al. |
| 5,823,198 A | 10/1998 | Jones et al. | 6,296,632 B1 | 10/2001 | Luscher et al. |
| 5,827,502 A | 10/1998 | Klaveness et al. | 6,306,418 B1 | 10/2001 | Bley |
| 5,827,531 A | 10/1998 | Morrison et al. | 6,306,419 B1 | 10/2001 | Vachon et al. |
| 5,830,178 A | 11/1998 | Jones et al. | 6,306,427 B1 | 10/2001 | Annonier et al. |
| 5,833,361 A | 11/1998 | Funk | 6,312,407 B1 | 11/2001 | Zadno-Azizi et al. |
| 5,840,387 A | 11/1998 | Berlowitz-Tarrant et al. | 6,315,709 B1 | 11/2001 | Garibaldi et al. |
| 5,846,518 A | 12/1998 | Yan et al. | 6,322,576 B1 | 11/2001 | Wallace et al. |
| 5,853,752 A | 12/1998 | Unger et al. | 6,335,384 B1 | 1/2002 | Evans et al. |
| 5,855,615 A | 1/1999 | Bley et al. | 6,344,182 B1 | 2/2002 | Sutton et al. |
| 5,863,957 A | 1/1999 | Li et al. | 6,355,275 B1 | 3/2002 | Klein |
| 5,876,372 A | 3/1999 | Grabenkort et al. | 6,368,658 B1 | 4/2002 | Schwarz et al. |
| 5,877,224 A | 3/1999 | Brocchini et al. | 6,379,373 B1 | 4/2002 | Sawhney et al. |
| 5,885,216 A | 3/1999 | Evans, III et al. | 6,388,043 B1 | 5/2002 | Langer et al. |
| 5,885,547 A | 3/1999 | Gray | 6,394,965 B1 | 5/2002 | Klein |
| 5,888,546 A | 3/1999 | Ji et al. | 6,423,332 B1 | 7/2002 | Huxel et al. |
| 5,891,130 A | 4/1999 | Palermo et al. | 6,432,437 B1 | 8/2002 | Hubbard |
| 5,891,155 A | 4/1999 | Irie | 6,436,112 B2 | 8/2002 | Wensel et al. |
| 5,894,022 A | 4/1999 | Ji et al. | 6,443,941 B1 | 9/2002 | Slepian et al. |
| 5,895,385 A | 4/1999 | Guglielmi et al. | 6,476,069 B2 | 11/2002 | Krall et al. |
| 5,895,398 A | 4/1999 | Wensel et al. | 6,544,503 B1 | 4/2003 | Vanderhoff et al. |
| 5,895,411 A | 4/1999 | Irie | 6,544,544 B2 | 4/2003 | Hunter et al. |
| 5,899,877 A | 5/1999 | Leibitzki et al. | 6,545,097 B2 | 4/2003 | Pinchuk et al. |
| 5,902,832 A | 5/1999 | Van Bladel et al. | 6,575,896 B2 | 6/2003 | Silverman et al. |
| 5,902,834 A | 5/1999 | Porrvik | 6,589,230 B2 | 7/2003 | Gia et al. |
| 5,922,025 A | 7/1999 | Hubbard | 6,602,261 B2 | 8/2003 | Greene, Jr. et al. |
| 5,922,304 A | 7/1999 | Unger | 6,602,524 B2 | 8/2003 | Batich et al. |
| 5,925,059 A | 7/1999 | Palermo et al. | 6,605,111 B2 | 8/2003 | Bose et al. |
| 5,928,626 A | 7/1999 | Klaveness et al. | 6,629,947 B1 | 10/2003 | Sahatjian et al. |
| 5,935,553 A | 8/1999 | Unger et al. | 6,632,531 B2 | 10/2003 | Blankenship |
| 5,951,160 A | 9/1999 | Ronk | 6,635,069 B1 | 10/2003 | Teoh et al. |
| 5,957,848 A | 9/1999 | Sutton et al. | 6,638,291 B1 | 10/2003 | Ferrera et al. |
| 5,959,073 A | 9/1999 | Schlameus et al. | 6,652,883 B2 | 11/2003 | Goupil et al. |
| 6,003,566 A | 12/1999 | Thibault et al. | 6,669,652 B2 | 12/2003 | Anderson et al. |
| 6,015,546 A | 1/2000 | Sutton et al. | 6,680,046 B1 | 1/2004 | Boschetti |
| 6,027,472 A | 2/2000 | Kriesel et al. | 6,699,222 B1 | 3/2004 | Jones et al. |
| 6,028,066 A | 2/2000 | Unger | 2001/0001835 A1 | 5/2001 | Greene, Jr. et al. |
| 6,047,861 A | 4/2000 | Vidal et al. | 2001/0016210 A1 | 8/2001 | Mathiowitz et al. |
| 6,048,908 A | 4/2000 | Kitagawa | 2001/0036451 A1 | 11/2001 | Goupil et al. |
| 6,051,247 A | 4/2000 | Hench et al. | 2001/0051670 A1 | 12/2001 | Goupil et al. |
| 6,056,721 A | 5/2000 | Shulze | 2002/0010481 A1* | 1/2002 | Jayaraman .................... 606/151 |
| 6,056,844 A | 5/2000 | Guiles et al. | 2002/0082499 A1 | 6/2002 | Jacobsen et al. |
| 6,059,766 A | 5/2000 | Greff | 2002/0197208 A1 | 12/2002 | Ruys et al. |
| 6,063,068 A | 5/2000 | Fowles et al. | 2003/0007928 A1 | 1/2003 | Gray |
| 6,071,495 A | 6/2000 | Unger et al. | 2003/0032935 A1 | 2/2003 | Damiano et al. |
| 6,071,497 A | 6/2000 | Steiner et al. | 2003/0040803 A1* | 2/2003 | Rioux et al. .................... 623/23.7 |
| 6,073,759 A | 6/2000 | Lamborne et al. | 2003/0108614 A1 | 6/2003 | Volkonsky et al. |

| | | | | | | |
|---|---|---|---|---|---|---|
| 2003/0183962 | A1 | 10/2003 | Buiser et al. | WO | WO 98/47532 | 10/1998 |
| 2003/0185895 | A1 | 10/2003 | Lanphere et al. | WO | WO 99/00187 | 1/1999 |
| 2003/0185896 | A1 | 10/2003 | Buiser et al. | WO | WO 99/12577 | 3/1999 |
| 2003/0187320 | A1 | 10/2003 | Freyman | WO | WO 99/42038 | 8/1999 |
| 2003/0194390 | A1 | 10/2003 | Krall et al. | WO | WO 99/43380 | 9/1999 |
| 2003/0203985 | A1 | 10/2003 | Baldwin et al. | WO | WO 99/57176 | 11/1999 |
| 2003/0206864 | A1 | 11/2003 | Mangin | WO | WO 00/23054 | 4/2000 |
| 2003/0215519 | A1 | 11/2003 | Schwarz et al. | WO | WO 00/32112 | 6/2000 |
| 2003/0233150 | A1 | 12/2003 | Bourne et al. | WO | WO 00/40259 | 7/2000 |
| 2004/0076582 | A1 | 4/2004 | DiMatteo et al. | WO | WO 00/53105 | 9/2000 |
| 2004/0091543 | A1 | 5/2004 | Bell et al. | WO | WO 00/71196 | 11/2000 |
| 2004/0092883 | A1 | 5/2004 | Casey, II et al. | WO | WO 00/74633 | 12/2000 |
| 2004/0096662 | A1 | 5/2004 | Lanphere et al. | WO | WO 01/12359 | 2/2001 |
| 2004/0101564 | A1 | 5/2004 | Rioux et al. | WO | WO 01/66016 | 9/2001 |
| 2004/0111044 | A1 | 6/2004 | Davis et al. | WO | WO 01/70291 | 9/2001 |
| 2004/0127919 | A1* | 7/2004 | Trout et al. .......... 606/157 | WO | WO 01/72281 | 10/2001 |
| 2004/0161451 | A1 | 8/2004 | Pierce et al. | WO | WO 01/76845 | 10/2001 |
| 2004/0181174 | A2 | 9/2004 | Davis et al. | WO | WO 01/93920 | 12/2001 |
| 2004/0186377 | A1 | 9/2004 | Zhong et al. | WO | WO 02/11696 | 2/2002 |
| 2005/0025800 | A1 | 2/2005 | Tan | WO | WO 02/34298 | 5/2002 |
| 2005/0037047 | A1 | 2/2005 | Song | WO | WO 02/34299 | 5/2002 |
| 2005/0095428 | A1 | 5/2005 | DiCarlo et al. | WO | WO 02/34300 | 5/2002 |
| 2005/0129775 | A1 | 6/2005 | Lanphere et al. | WO | WO 02/43580 | 6/2002 |
| 2005/0165366 | A1* | 7/2005 | Brustad et al. ......... 604/264 | WO | WO 02/96302 | 12/2002 |
| 2005/0196449 | A1 | 9/2005 | DiCarlo et al. | WO | WO 03/013552 | 2/2003 |
| 2005/0226935 | A1 | 10/2005 | Kamath et al. | WO | WO 03/051451 | 6/2003 |
| 2005/0238870 | A1 | 10/2005 | Buiser et al. | WO | WO 03/082359 | 10/2003 |
| 2005/0263916 | A1 | 12/2005 | Lanphere et al. | WO | WO 2004/019999 | 3/2004 |
| 2006/0079926 | A1* | 4/2006 | Desai et al. ........... 606/200 | WO | WO 2004/040972 | 5/2004 |
| | | | | WO | WO 2004/073688 | 9/2004 |
| | | | | WO | WO 2005/009253 | 2/2005 |

FOREIGN PATENT DOCUMENTS

| | | |
|---|---|---|
| DE | 3834705 | 4/1990 |
| DE | 94 14 868.6 | 12/1994 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 820 726 | 1/1998 |
| EP | 0 865 773 | 9/1998 |
| EP | 0 993 337 | 4/2000 |
| FR | 2 641 692 | 7/1990 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| TW | 421658 | 2/2001 |
| WO | WO 91/12823 | 5/1991 |
| WO | WO 92/21327 | 12/1992 |
| WO | WO 93/19702 | 10/1993 |
| WO | WO 94/06503 | 3/1994 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/22736 | 8/1996 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |

OTHER PUBLICATIONS

Abbara et al., "Transcervical Expulsion of a Fibroid as a Result of Uterine Artery Embolization for Leiomyomata", *JVIR*, vol. 10, No. 4, pp. 409-411, 1999.

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Ahuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D., et al., "Polyvinyl Alcohol Foam Particles Sizes and Concentrations Injectable through Microcatheters", *JVIR*, vol. 9, No. 1, pp. 113-118; 1998.

Barton, P. et al., "Embolization of Bone Metastases," *Journal of Vascular and Interventional Radiology*, 7(1):81-88 (Jan.-Feb. 1996).

Battinelli, L. et al., "New Class of Poly(vinyl alcohol) Polymrs as Column-Chromatography Stationary Phases for *Candida rugosa* Lipase Isoforms Separation", *J. Chromatogr A*, vol. 753, No. 1, pp. 47-55; 1996.

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Boston Scientific Target, IDC™ Interlocking Coil, 1 page.

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (Summary).

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al, "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997),http://home.texoma.net./~moreland/stats/hcc-9.html.

Concentric Medical, Inc.—Product Information (3 pages), 2002.

Cruise et al., "In Vitro and In Vivo Characterization of a Hydrogel-Based Aneurysm Embolization System," *Society for Biomaterials 28$^{th}$ Annual Meeting Transactions*, p. 203 (2002).

Deasy, P. B., *"Microencapsulation and Related Drug Processes"*, New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

Duckwiler et al., "Catheters, embolic agents spark neurointervention," *Diagnostic Imaging*, 16(5):66-72 (May 1994).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", Radiology, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Guglielmi Detachable Coils (GDC); http://www.neurosurgery.pitt.edu/endovascular/treatments/gdc.html, Jun. 2005, pp. 1-3.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*, 17:1901-1906 (Nov. 1996).

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Horak et al., "Hydrogels in endovascular embolization. 1. Spherical particles of poly (2-hydroxyethyl methacrylate) and their medico-biological properties", *Biomaterials*, 7(3):188-192 (May 1986).

Horak et al., "Hydrogels in endovascular embolization. H. Clinical use of spherical particles", *Biomaterials*, 7(6):467-470 (Nov. 1986).

Huang, et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (Abstract).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet9l/scipro/ppr472.htm, Mar. 12, 1991.

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Kim, et al., "Composite poly(vinyl alcohol) beads for controlled drug delivery", *Pharm Res*, vol. 9. No. 1, pp. 10-16, 1992.

Kim et al., "Poly(vinyl alcohol) beads with core-shell structure for drug delivery," *Cosmetic and Pharmaceutical Applications of Polymers*, Plenum Press, New York, pp. 209-214 (1991).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992 (Abstract).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (Abstract).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (Abstract).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization," http://www.uhmc.edu/dotter-fibroid, 34 pages.

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm, 2 pages.

Purdy, et al., "Arteriovenous malformations of the brain: choosing embolic materials to enhance safety and ease of excision", *J Neurosurg*, vol. 77, No. 2, pp. 217-222, 1992.

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (abstract).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Nagle. Med.*, vol. 181, No. 2, pp. 233-246, Feb. 4, 1997 (Summary).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/prlit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tamatani et al., "Radiologic and Histopathologic Evaluation of Canine Artery Occlusion after Collagen-Coated Platinum Microcoil Delivery," *American Journal of Neuroradiology*, 20:541-545 (1999).

Tanaka et al., "Radiologic Placement of Side-Hole Catheter With Tip Fixation for Hepatic Arterial Infusion Chemotherapy," *JVIR*, vol. 4, pp. 63-68, 2003.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (Abstract).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variocotocele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (Abstract).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part 1—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wrtrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

Bhattacharya et al., "Research & Aneurysms," *Interventional Neuroradiology*, 11(Suppl. 2):87-94 (Oct. 2005).

Bracard et al., "AVMs," *Interventional Neuroradiology*, 11(Suppl. 2):178-184 (Oct. 2005).

Collice et al., "Neurosurgery & Aneurysms," *Interventional Neuroradiology*, 11(Suppl. 2):226-231 (Oct. 2005).

Cotroneo et al., "Aneurysms," *Interventional Neuroradiology*, 11(Suppl. 2):212-216 (Oct. 2005).

Ducati et al., "Aneurysms," *Interventional Neuroradiology*, 11(Suppl. 2):95-99 (Oct. 2005).

Hon-Man et al., "Miscellanea," *Interventional Neuroradiology*, 11(Suppl. 2):159-164 (Oct. 2005).

"How Matrix™ Detachable Coils Work," 1 page.

Kallmes et al., "Platinum Coil-mediated Implantation of Growth Factor-secreting Endovascular Tissue Grafts: An in Vivo Study," *Radiology*, 207(2):519-523 (May 1998).

Kominami et al., "Complications," *Interventional Neuroradiology*, 11(Suppl. 2):191-195 (Oct. 2005).

"Matrix® Detachable Coils," Boston Scientific, http://www.bostonscientific.com, 3 pages (Retrieved from the Internet on Jul. 13, 2005).

"Micrus Corporation Announces Encouraging Results of a Modified Coil, Cerecyte, for the Treatment of Cerebral Aneurysms," Business Wire, 2 pages (Nov. 19, 2003).

Pasquini et al., "Aneurysms," *Interventional Neuroradiology*, 11(Suppl. 2):136-143 (Oct. 2005).

U.S. Appl. No. 11/274,538, filed Nov. 15, 2005, Tenney et al.

Pérez Higueras et al., "Fistulae," *Interventional Neuroradiology*, 11(Suppl. 2):123-129 (Oct. 2005).

Piske et al., "CT & MRI," *Interventional Neuroradiology*, 11(Suppl. 2):100-106 (Oct. 2005).

Sellar et al., "Fistulae," *Interventional Neuroradiology*, 11 (Suppl. 2):130-135 (Oct. 2005).

Strother et al., "Aneurysms," *Interventional Neuroradiology*, 11(Suppl. 2):200-205 (Oct. 2005).

Tournade et al., "Miscellanea," *Interventional Neuroradiology*, 11(Suppl. 2):107-111 (Oct. 2005).

Cekirge et al., "Interlocking Detachable Coil Occlusion in the Endovascular Treatment of Intracranial Aneurysms: Preliminary Results," *AJNR Am. J. Neuroradiol.*, 17:1651-1657 (Oct. 1996).

Marks et al., "A Mechanically Detachable Coil for the Treatment of Aneurysms and Occlusion of Blood Vessels," *AJNR Am. J. Neuroradiol.*, 15:821-827 (May 1994).

Murphy, "Endovascular procedures," Johns Hopkins Interventional Neuroradiology [online], http://www.brainaneurysms.net/procedures/neurovasc_aneurysm.htm, 2 pages (retrieved from the Internet on Feb. 17, 2005).

Murphy et al., "Mechanical Detachable Platinum Coil: Report of the European Phase II Clinical Trial in 60 Patients," *Radiology*, 219:541-544 (2001).

"Providing Superior Coils, Components, and Assemblies for Medical Devices," Heraeus Vadnais, Inc. [online], http://www.vadtec.com, 6 pages (retrieved from the Internet on Feb. 22, 2005).

* cited by examiner

EMBOLIC COILS

TECHNICAL FIELD

The invention relates to embolic coils, as well as related methods, devices, and compositions.

BACKGROUND

Therapeutic vascular occlusions (embolizations) are used to prevent or treat pathological conditions in situ. Embolic coils can be used to occlude vessels in a variety of medical applications. Delivery of embolic coils (e.g., through a catheter) can depend on the size and/or shape of the coils. Some embolic coils include fibers that can, for example, enhance thrombosis at a treatment site.

SUMMARY

In one aspect, the invention features an embolic coil that includes a wire having a primary shape with a first outer diameter and a second outer diameter that is smaller than the first outer diameter. The embolic coil is configured to fit within the lumen of a subject.

In another aspect, the invention features a method of making an embolic coil, the method including forming a wire into a primary shape with a first outer diameter and a second outer diameter that is smaller than the first outer diameter to form the embolic coil.

In another aspect, the invention features a medical device that includes a tubular body (e.g., a catheter) with a lumen, and at least one embolic coil (e.g., multiple embolic coils) disposed within the lumen. The embolic coil includes a wire that has a primary shape with a first outer diameter and a second outer diameter that is smaller than the first outer diameter.

In another aspect, the invention features a method that includes administering at least one embolic coil (e.g., multiple embolic coils) to a subject. The embolic coil includes a wire that has a primary shape with a first outer diameter and a second outer diameter that is smaller than the first outer diameter.

In another aspect, the invention features a method of using a medical device that includes a tubular body (e.g., a catheter) with a lumen, and at least one embolic coil (e.g., multiple embolic coils) disposed within the lumen. The embolic coil includes a wire that has a primary shape with a first outer diameter and a second outer diameter that is smaller than the first outer diameter. The method includes inserting the tubular body into the lumen of a subject, and delivering the embolic coil into the lumen of the subject.

Embodiments may also include one or more of the following.

The embolic coil can have an effective column strength of from 0.005 pound to about 0.05 pound.

The first outer diameter can be at most about 0.03 inch (e.g., from about 0.014 inch to about 0.016 inch), and/or the second outer diameter can be at most about 0.025 inch (e.g., from about 0.012 inch to about 0.013 inch). In some embodiments, the difference between the first outer diameter and the second outer diameter can be at most about 0.024 inch (e.g., from 0.001 inch to 0.004 inch). In certain embodiments, the ratio of the first outer diameter to the second outer diameter can be at least about 1.05:1, and/or at most about 1.5:1. For example, the ratio of the first outer diameter to the second outer diameter can be from about 1.05:1 to about 1.5:1.

In some embodiments, a region of the wire that has the first outer diameter can have a length of at most about 35 centimeters. In certain embodiments, a region of the wire that has the second outer diameter can have a length of at most about 10 millimeters (e.g., at most about five millimeters).

The wire can have a diameter of from 0.001 inch to 0.005 inch (e.g., 0.003 inch), and/or a restrained length of at most about 250 inches. The wire in its primary shape can have a length that is at least about 20 centimeters. The wire can include a metal (e.g., platinum). The wire can have a secondary shape, such as a J, a diamond, a vortex, or a spiral.

The embolic coil can include at least one fiber that is attached (e.g., tied) to the wire (e.g., to a region of the wire that has the second outer diameter). The fiber can include polyethylene terephthalate and/or nylon. In certain embodiments, the fiber can have a length of from about 0.5 millimeter to about five millimeters.

Forming a wire into a primary shape can include applying a temperature of about 25° C. to the wire and/or winding the wire around a mandrel. The mandrel can have a third outer diameter and a fourth outer diameter that is smaller than the third outer diameter. In some embodiments, the third outer diameter can be at most about 0.03 inch. In certain embodiments, the fourth outer diameter can be at most about 0.025 inch. The mandrel can include stainless steel. The mandrel can have a lubricious coating (e.g., including polytetrafluoroethylene). The mandrel can include a shape-memory material. In some embodiments, the mandrel can be formed of an erodible or dissolvable material (e.g., an erodible or dissolvable polymer, metal, or metal alloy). In certain embodiments, the mandrel can be hollow.

The method can further include attaching (e.g., bonding) at least one fiber to the wire (e.g., to a region of the wire having the second outer diameter). In some embodiments, the fiber can be attached to the wire by compressing the fiber between a first winding of the wire and a second winding of the wire. In certain embodiments, the fiber can be adhesive bonded to the wire.

Forming a wire into a primary shape can include applying a first tension to the wire to wind a first region of the wire around a mandrel, and applying a second tension to the wire to wind a second region of the wire around the mandrel. The second tension can be greater than the first tension. In some embodiments, the first tension can be from about four grams to about 80 grams (e.g., from about 10 grams to about 80 grams, from about 25 grams to about 29 grams). In certain embodiments, the second tension can be from about 15 grams to about 100 grams (e.g., from about 30 grams to about 40 grams). The difference between the second tension and the first tension can be from about five grams to about 90 grams.

The method can further include forming the wire into a secondary shape (e.g., a J, a diamond, a vortex, or a spiral). Forming the wire into a secondary shape can include applying a temperature of about 1100° F. to the wire and/or winding the wire in its primary shape around a mandrel. The mandrel can be a stainless steel mandrel. In some embodiments, the mandrel can be plated with chrome.

The method can further include combining the embolic coil with a pharmaceutically acceptable medium.

The medical device can include a pusher wire. In some embodiments, the pusher wire can be disposed within the lumen of the tubular member or tubular body, and attached to the embolic coil.

In some embodiments, the method of administration can be by a catheter. In certain embodiments, the method of administration can be by a device that has an internal opening, and that is configured to fit within a lumen of a subject. The embolic coil can be disposed within the internal opening of the device.

The method can further include using a pusher and/or a saline flush to deliver the embolic coil from the device. In some embodiments, the method can be used to treat aneurysms, arteriovenous malformations, traumatic fistulae, tumors, and combinations thereof. In certain embodiments, the method can include embolizing a lumen of a subject. In some embodiments, the embolic coil can be used in a transarterial chemoembolization procedure. Delivering the embolic coil into the lumen of the subject can include detaching (e.g., chemically detaching, electrolytically detaching) the embolic coil from the pusher wire. The embolic coil can be mechanically detached from the pusher wire. In some embodiments, the method can further include withdrawing the embolic coil into the lumen of the tubular body.

Embodiments can include one or more of the following advantages.

In some embodiments, an embolic coil can exhibit relatively good occlusive properties when delivered to a location of interest within a subject. This can, for example, allow the embolic coil to be used to occlude a vessel (e.g., to embolize a tumor), treat an aneurysm, treat an arteriovenous malformation, and/or treat a traumatic fistula.

In certain embodiments, an embolic coil can have a relatively low likelihood of sticking to the wall of a delivery catheter. This can, for example, reduce the possibility of complications resulting from the embolic coil sticking to the wall of the delivery catheter when the embolic coil is being delivered to a location of interest within a subject.

In some embodiments, an embolic coil can have a relatively high effective column strength. This can, for example, allow the embolic coil to be delivered to a location of interest within a subject even if the embolic coil undergoes some sticking to the wall of the delivery catheter during delivery of the embolic coil.

In certain embodiments, an embolic coil can have a relatively low likelihood of sticking to the wall of a delivery catheter, while also exhibiting relatively good occlusive properties when delivered to a location of interest within a subject.

In some embodiments, an embolic coil can have a relatively high effective column strength, while also exhibiting relatively good occlusive properties when delivered to a location of interest within a subject.

In certain embodiments, an embolic coil can have a relatively low likelihood of sticking to the wall of a delivery catheter, while also having a relatively high effective column strength, so that even if the embolic coil does stick to the wall of the delivery catheter, the coil can be pushed to a sufficient extent to overcome the sticking and deliver the coil from the catheter.

In some embodiments, an embolic coil can have a relatively low likelihood of sticking to the wall of a delivery catheter, a relatively high effective column strength, and relatively good occlusive properties when delivered to a location of interest within a subject.

Features and advantages are in the description, drawings, and claims.

DETAILED DESCRIPTION

Figure 1A:
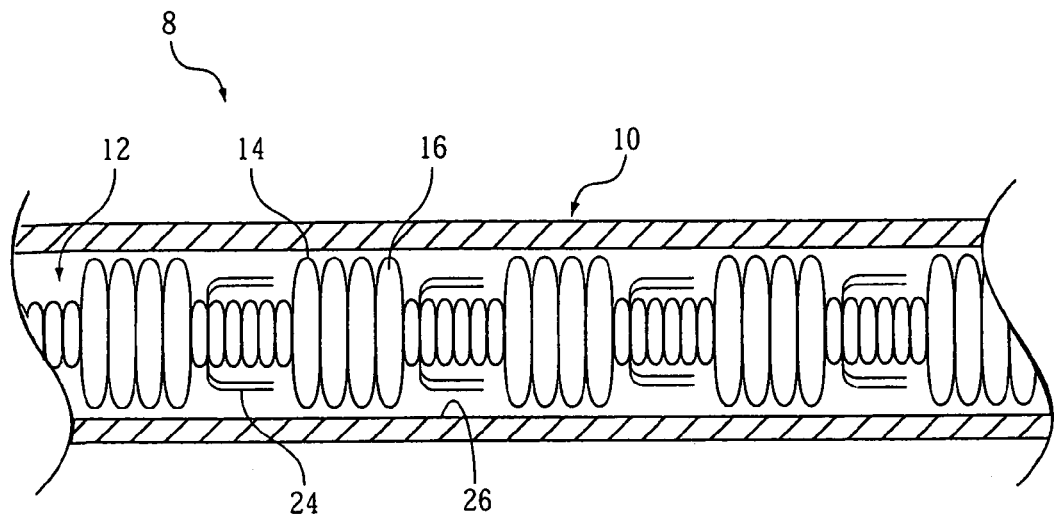
FIG. 1A is a side view of an embodiment of an embolic coil in a delivery device.
Figure 1B:
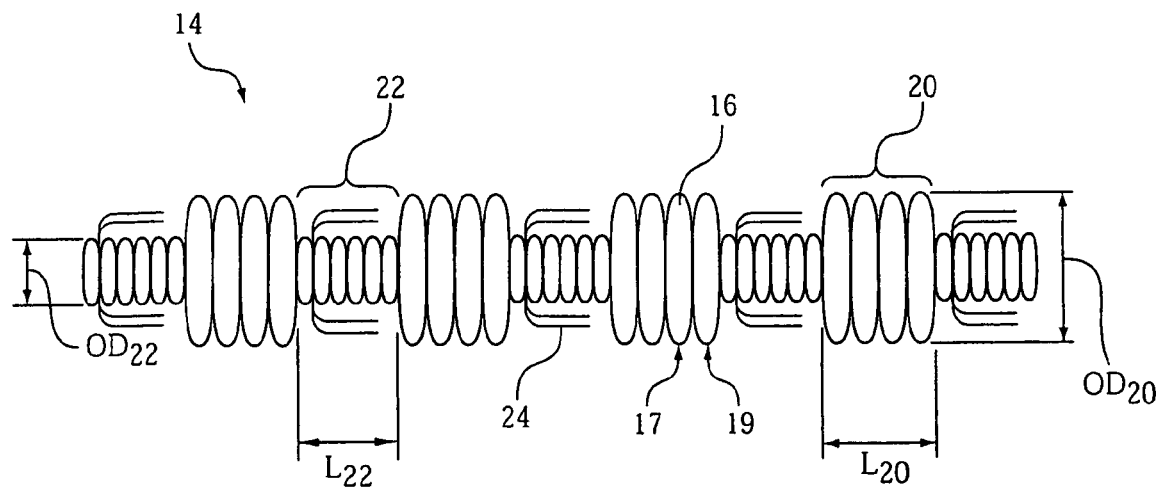
FIG. 1B is a side view of the embolic coil of FIG. 1A.

FIG. 1A shows an embolic coil delivery system 8, which includes a catheter 10 with a lumen 12. An embolic coil 14, formed out of a wire 16, is disposed within lumen 12. As FIG. 1B shows, embolic coil 14 includes regions 20 of relatively large outer diameter and regions 22 of relatively small outer diameter, to which fibers 24 are attached. Regions 20 have an outer diameter "$OD_{20}$" and a length "$L_{20}$", and regions 22 have an outer diameter "$OD_{22}$" and a length "$L_{22}$". Because fibers 24 are attached to wire 16 in regions 22 of relatively small outer diameter, embolic coil 14 can be accommodated within lumen 12 of catheter 10, with a relatively low likelihood of substantial contact between fibers 24 and wall 26 of lumen 12. This can be advantageous, for example, because if fibers 24 come into sufficient contact with wall 26, then fibers 24 can adhere to wall 26, which can complicate the delivery of embolic coil 14 from catheter 10 to a treatment site.

In general, the design of embolic coil 14 can result in embolic coil 14 having a relatively high effective column strength. The effective column strength of embolic coil 14 is the column strength (the compression load at which embolic coil 14 will buckle) of embolic coil 14 when embolic coil 14 is constrained within lumen 12 of catheter 10. The presence of regions 20 of relatively large outer diameter in embolic coil 14 can limit the likelihood that embolic coil 14 will buckle, because outer diameter "$OD_{20}$" of regions 20 can be selected such that regions 20 are relatively close to wall 26 of catheter 10. Because embolic coil 14 has a relatively high effective column strength, embolic coil 14 can also have good pushability. Thus, even if fibers 24 adhere to wall 26 of lumen 12, embolic coil 14 may be sufficiently pushable to overcome the adhesion. Furthermore, an embolic coil with a relatively high effective column strength can, for example, be less likely to buckle during deployment from a delivery device than a comparable embolic coil with a relatively low effective column strength. In some embodiments (e.g., embodiments in which outer diameter "$OD_{20}$" is about 0.012 inch or about 0.035 inch), embolic coil 14 can have an effective column strength of at least 0.005 pound (e.g., at least 0.007 pound, at least about 0.01 pound, at least about 0.03 pound), and/or at most about 0.05 pound (e.g., at most about 0.03 pound, at most about 0.01 pound, at most 0.007 pound).

In general, outer diameter "$OD_{20}$", the relatively large outer diameter, is selected to provide strength to embolic coil 14, while also allowing embolic coil 14 to fit within lumen 12 of catheter 10. In some embodiments, outer diameter "$OD_{20}$" can be at most about 0.03 inch. In certain embodiments (e.g., for an intermediate-sized embolic coil), outer diameter "$OD_{20}$" can be from about 0.014 inch to about 0.016 inch (e.g., from about 0.014 inch to about 0.015 inch). In some embodiments (e.g., for a relatively small embolic coil), outer diameter "$OD_{20}$" can be at most about 0.01 inch.

Generally, outer diameter "$OD_{22}$", the relatively small outer diameter, is selected to accommodate fibers 24 and to limit the amount of contact between fibers 24 and wall 26 of lumen 12. In certain embodiments, outer diameter "$OD_{22}$" can be at most about 0.025 inch. In some embodiments (e.g., for a relatively large embolic coil), outer diameter "$OD_{22}$" can be from about 0.012 inch to about 0.021 inch (e.g., from about 0.012 inch to about 0.013 inch, from about 0.019 inch to about 0.021 inch). In certain embodiments (e.g., for an intermediate-sized embolic coil), outer diameter "$OD_{22}$" can be from about 0.01 inch to about 0.012 inch. In some embodiments (e.g., for a relatively small embolic coil), outer diameter "$OD_{22}$" can be from 0.006 inch to 0.008 inch.

Typically, as the difference between outer diameter "$OD_{20}$" and outer diameter "$OD_{22}$" increases, longer fibers may be accommodated on embolic coil 14. In general, as the difference between outer diameter "$OD_{20}$" and outer diameter "$OD_{22}$" decreases, the likelihood of kinking by embolic coil 14 may decrease. In embodiments, the difference between outer diameter "$OD_{20}$" and outer diameter "$OD_{22}$" typically can be at most about 0.024 inch (e.g., at most about 0.01 inch). For example, the difference between outer diameter "$OD_{20}$" and outer diameter "$OD_{22}$" can be from 0.001 inch to 0.004 inch (e.g., from 0.001 inch to 0.003 inch).

Generally, as the ratio of outer diameter "$OD_{20}$" to outer diameter "$OD_{22}$" increases, longer fibers may be accommodated on embolic coil 14. Typically, as the ratio of outer diameter "$OD_{20}$" to outer diameter "$OD_{22}$" decreases, the likelihood of kinking by embolic coil 14 may decrease. In some embodiments, the ratio of outer diameter "$OD_{20}$" to outer diameter "$OD_{22}$" can be at least about 1.05:1 (e.g., at least about 1.08:1, at least about 1.2:1, at least about 1.25:1, at least about 1.4:1), and/or at most about 1.5:1 (e.g., at most about 1.4:1, at most about 1.25:1, at most about 1.2:1, at most about 1.08:1). In certain embodiments, the ratio of outer diameter "$OD_{20}$" to outer diameter "$OD_{22}$" can be from about 1.05:1 to about 1.5:1 (e.g., from about 1.2:1 to about 1.4:1).

While lengths "$L_{20}$" and "$L_{22}$" can generally be selected as desired, in some embodiments lengths "$L_{20}$" and "$L_{22}$" can be selected to achieve certain properties (e.g., effective column strength). In general, as the ratio of "$L_{20}$" to "$L_{22}$" increases, the effective column strength of embolic coil 14 increases. Alternatively or additionally, fibers 24 may be more protected from over-exposure to blood during delivery, thereby resulting in a decrease in the occurrence of premature thrombosis. Typically, as the ratio of "$L_{20}$" to "$L_{22}$" decreases, the effective column strength of embolic coil 14 can decrease. Generally, as the difference between "$L_{20}$" and "$L_{22}$" increases, the effective column strength of embolic coil 14 can increase. In general, as the difference between "$L_{20}$" and "$L_{22}$" decreases, the effective column strength of embolic coil 14 can decrease.

In some embodiments, length "$L_{20}$" can be at least about 0.4 centimeter (e.g., at least about one centimeter, at least about two centimeters, at least about five centimeters, at least about 10 centimeters, at least about 20 centimeters, at least about 30 centimeters), and/or at most about 35 centimeters (e.g., at most about 30 centimeters, at most about 20 centimeters, at most about 10 centimeters, at most about five centimeters, at most about two centimeters, at most about one centimeter). For example, length "$L_{20}$" can be from about 0.4 centimeter to about 20 centimeters (e.g., from about one centimeter to about 20 centimeters, from about five centimeters to about 10 centimeters).

In certain embodiments, length "$L_{22}$" can be at least about 0.5 millimeter (e.g., at least about one millimeter, at least about two millimeters, at least about 2.5 millimeters, at least about three millimeters, at least about four millimeters, at least about five millimeters, at least about eight millimeters), and/or at most about 10 millimeters (e.g., at most about eight millimeters, at most about five millimeters, at most about four millimeters, at most about three millimeters, at most about 2.5 millimeters, at most about two millimeters, at most about one millimeter). For example, length "$L_{22}$" can be from about one millimeter to about two millimeters.

The length of embolic coil 14 when fully extended within lumen 12 of catheter 10 generally can be selected to allow embolic coil 14 to fit within a delivery device such as catheter 10. In some embodiments embolic coil 14 can be relatively long yet still exhibit good effective column strength so that, for example, even though embolic coil 14 is long, it is sufficiently stiff to be delivered with little or no buckling. In some embodiments, a relatively long embolic coil (which can also exhibit good effective column strength) can be used instead of multiple shorter embolic coils. In some instances, using a single relatively long embolic coil rather than multiple shorter embolic coils can, for example, reduce the time associated with an embolization procedure, increase the efficiency of an embolization procedure, and/or reduce the likelihood of complications associated with an embolization procedure. In certain embodiments, embolic coil 14 can have a fully extended length of at least about 0.5 centimeter (e.g., at least about 2.3 centimeters, at least about five centimeters, at least about 10 centimeters, at least about 15 centimeters, at least about 20 centimeters, at least about 30 centimeters), and/or at most about 40 centimeters (e.g., at most about 30 centimeters, at most about 20 centimeters, at most about 15 centimeters, at most about 10 centimeters, at most about five centimeters, at most about 2.3 centimeters). In certain embodiments, embolic coil 14 can have a fully extended length of from about 0.5 centimeter to about 40 centimeters (e.g., from about 2.3 centimeters to about 30 centimeters, from about five centimeters to about 25 centimeters).

As shown in FIG. 1B, embolic coil 14 is formed of windings of wire 16, such as windings 17 and 19. In general, there is little to no space between consecutive windings (e.g., windings 17 and 19) of embolic coil 14. Fibers 24 are tightly fitted between consecutive windings within regions 22 of embolic coil 14.

The pitch of an embolic coil is the sum of the thickness of one winding of wire 16 (e.g., winding 17) and the amount of space between that winding and a consecutive winding (e.g., winding 19). In some embodiments, embolic coil 14 can have a pitch of at most about 0.01 inch (e.g., about 0.003 inch). Because the windings of embolic coil 14 are flush with each other, the pitch of embolic coil 14 is equal to the diameter of wire 16.

The diameter of wire 16 can be selected, for example, based on the desired properties (e.g., size, strength) and/or applications of embolic coil 14. In some embodiments, wire 16 can have a diameter of from 0.001 inch to 0.005 inch (e.g., from 0.0015 inch to 0.005 inch, from 0.002 inch to 0.003 inch, from 0.00225 inch to 0.003 inch). In certain embodiments, wire 16 can have a diameter of 0.003 inch. In some embodiments (e.g., embodiments in which embolic coil 14 is used for peripheral vascular applications), wire 16 can have a diameter of at least about 0.004 inch. In certain embodiments (e.g., embodiments in which embolic coil 14 is used for neurological applications), wire 16 can have a diameter of at most about 0.002 inch. Alternatively or additionally, wire 16 can have a restrained length of at most about 250 inches (e.g., at most about 200 inches, at most about 185 inches, at most about 150 inches, at most about 100 inches, at most about 50 inches).

Wire 16 can be formed of, for example, one or more metals or metal alloys, such as platinum, a platinum alloy (e.g., a platinum-tungsten alloy), stainless steel, nitinol, and Elgiloy® (from Elgiloy Specialty Metals).

Fibers 24 are typically formed of one or more materials that can enhance thrombosis (e.g., at a target site). Examples of materials from which fibers 24 can be made include polyethylene terephthalate (e.g., Dacron®), nylon, and collagen. Fibers 24 can have a length of from about 0.5 millimeter to about five millimeters (e.g., about 2.5 millimeters). In some embodiments, the length of fibers 24 can be selected so that fibers 24 can fit within regions 22 of relatively small outer diameter without bunching up.

Embolic coils can generally be used in a number of different applications, such as neurological application and/or peripheral applications. In some embodiments, embolic coils can be used to occlude a vessel, and/or to treat an aneurysm (e.g., an intercranial aneurysm), an arteriovenous malformation (AVM), or a traumatic fistula. In some embodiments, embolic coils can be used to embolize a tumor (e.g., a liver tumor). In certain embodiments, embolic coils can be used in transarterial chemoembolization (TACE).

Figure 2A:
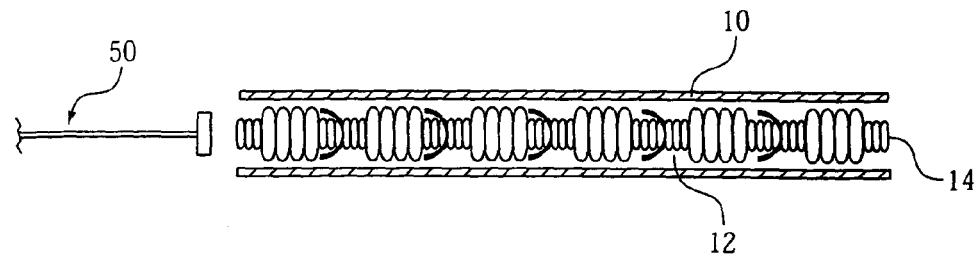
FIGS. 2A-2C illustrate the delivery of an embodiment of an embolic coil to the site of an aneurysm.
Figure 2B:
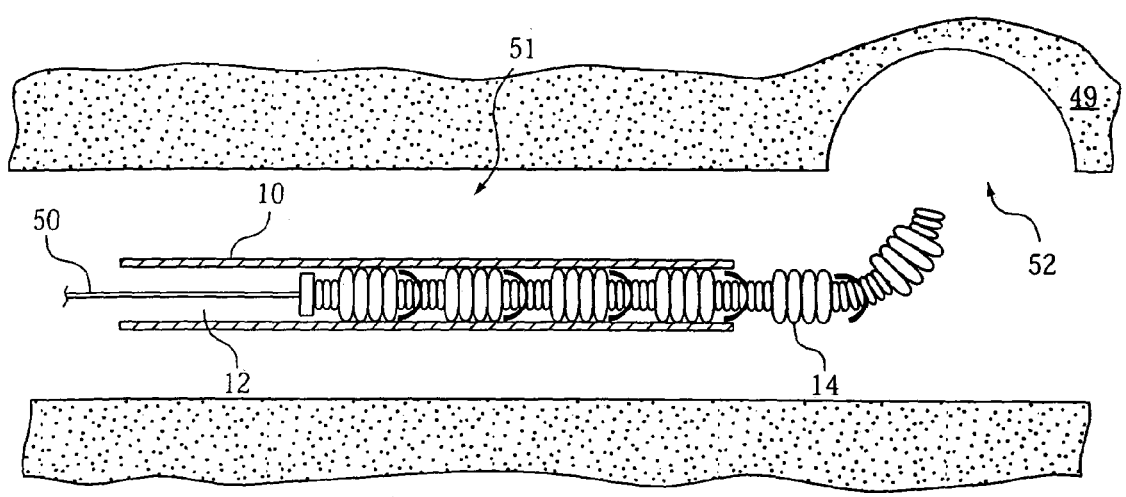
Figure 2C:
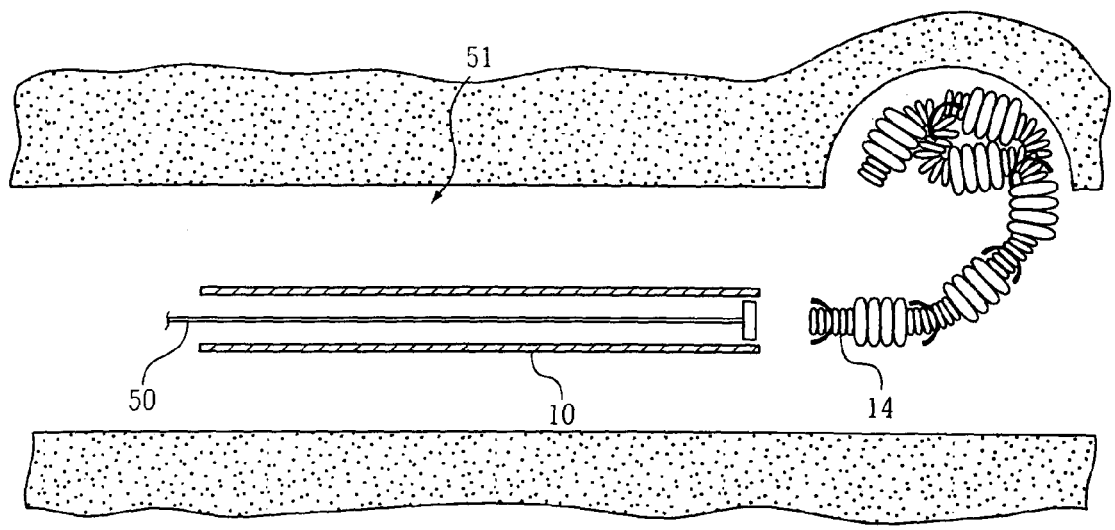

FIGS. 2A-2C show the use of embolic coil 14 to fill and occlude an aneurysmal sac. FIG. 2A shows embolic coil 14, loaded into lumen 12 of catheter 10, and a pusher wire 50 disposed outside of catheter 10. In some embodiments, embolic coil 14 can be disposed within a carrier fluid (e.g., a saline solution, a contrast agent, a heparin solution) while embolic coil 14 is within lumen 12 of catheter 10. In FIG. 2B, catheter 10 is delivered into a lumen 51 of a subject, and pusher wire 50 is inserted into lumen 12 of catheter 10, such that it contacts embolic coil 14. Pusher wire 50 is then used to push embolic coil 14 out of catheter 10, into lumen 51, and toward an aneurysmal sac 52 formed in wall 49 of lumen 51. FIG. 2C shows embolic coil 14 filling aneurysmal sac 52 after embolic coil 14 has been pushed out of catheter 10 by pusher wire 50. By filling aneurysmal sac 52, embolic coil 14 helps to occlude aneurysmal sac 52. This occlusion of aneurysmal sac 52 can be accelerated by fibers 24, which can enhance thrombosis within aneurysmal sac 52. An accelerated embolization procedure can benefit the subject by, for example, reducing exposure time to fluoroscopy.

In general, embolic coil 14 has a primary shape and a secondary shape. Embolic coil 14 exhibits only its primary shape when embolic coil 14 is fully extended within lumen 12 of catheter 10 (as shown in FIG. 1A). As embolic coil 14 exits catheter 10, however, embolic coil 14 further assumes its secondary shape, which allows embolic coil 14 to fill aneurysmal sac 52. Typically, the primary shape of embolic coil 14 is selected for deliverability, and the secondary shape of embolic coil 14 is selected for application (e.g., embolization of an aneurysm).

Figure 3A:
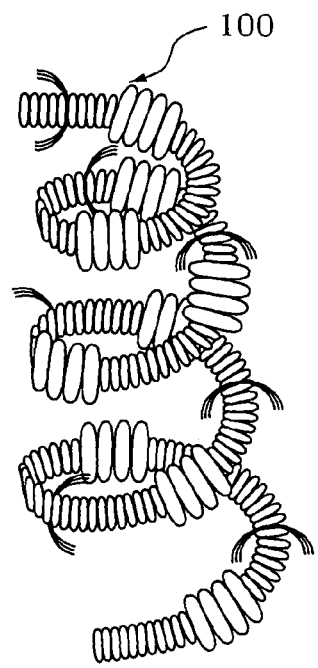
FIG. 3A is a perspective view of an embodiment of an embolic coil.
Figure 3B:
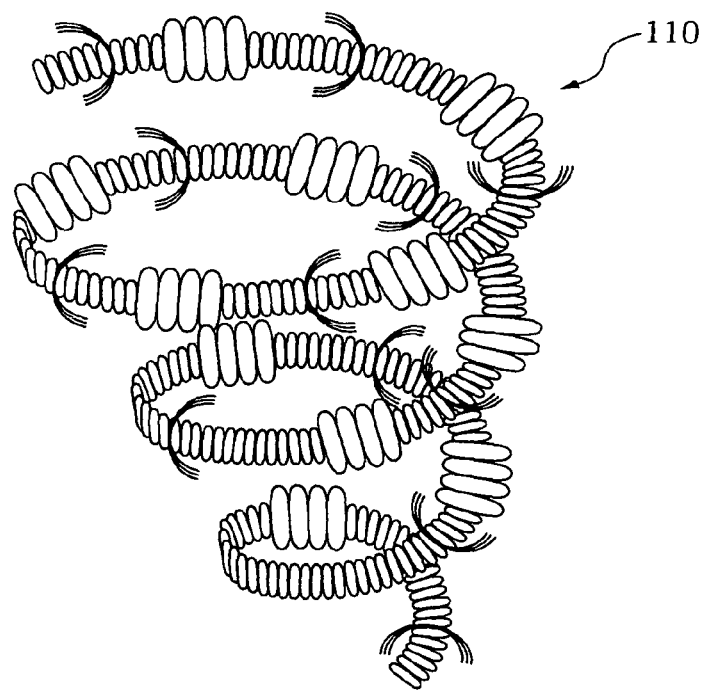
FIG. 3B is a perspective view of an embodiment of an embolic coil.
Figure 3C:
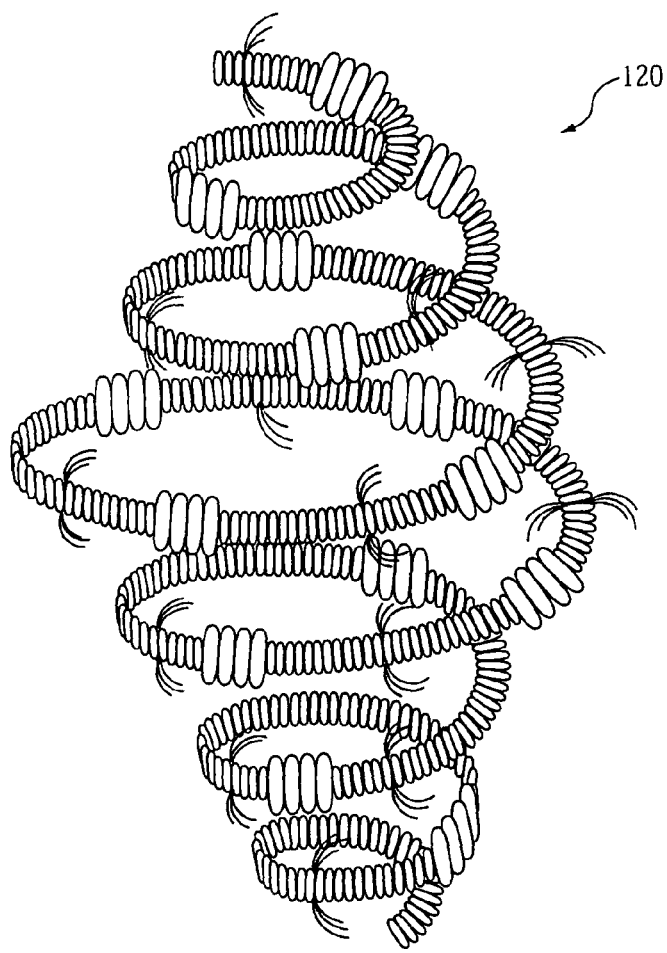
FIG. 3C is a perspective view of an embodiment of an embolic coil.
Figure 3D:
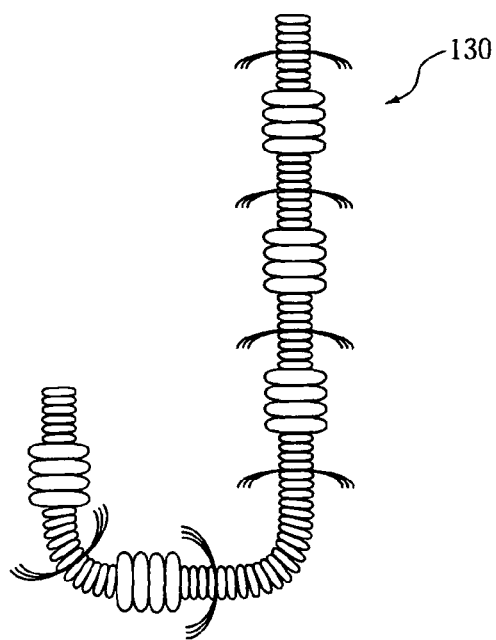
FIG. 3D is a perspective view of an embodiment of an embolic coil.

As FIGS. 3A-3D illustrate, an embolic coil can have any of a number of different secondary shapes, which can depend on the particular application for the embolic coil. For example, FIG. 3A shows an embolic coil 100 with a spiral secondary shape, which can be used, for example, to provide a supportive framework along a vessel wall. Alternatively or additionally, an embolic coil with a spiral secondary shape can be used to hold other embolic coils that are subsequently delivered to the target site. FIG. 3B shows an embolic coil 110 with a vortex secondary shape, which can be used, for example, to close the center of a target site (e.g., a vessel or an aneurysm) that is to be occluded, and/or to occlude a target site in conjunction with an embolic coil such as embolic coil 100 (FIG. 3A). As shown in FIG. 3C, an embolic coil 120 can have a diamond secondary shape, which, like the vortex secondary shape, can used, for example, to close the center of a target site (e.g., a vessel or an aneurysm) that is to be occluded, and/or to occlude a target site in conjunction with an embolic coil such as embolic coil 100 (FIG. 3A). FIG. 3D shows an embolic coil 130 with a secondary shape in the form of a J, which can be used, for example, to fill remaining space in an aneurysm that was not filled by other coils. In some embodiments, an operator (e.g., a physician) can hook the curved portion of embolic coil 130 into a coil or coil mass that has already been deployed at a target site, and then shape the straighter portion of coil 130 to fill the target site.

Figure 4A:
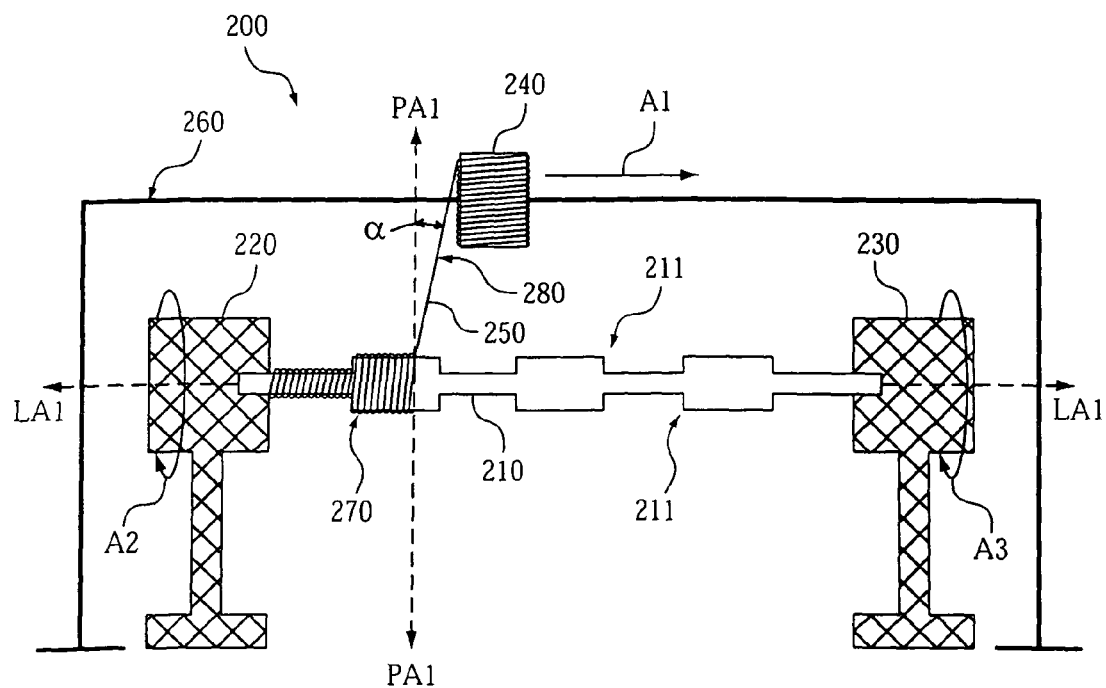
FIG. 4A is a side view of an embodiment of a process for forming an embolic coil.
Figure 5A:
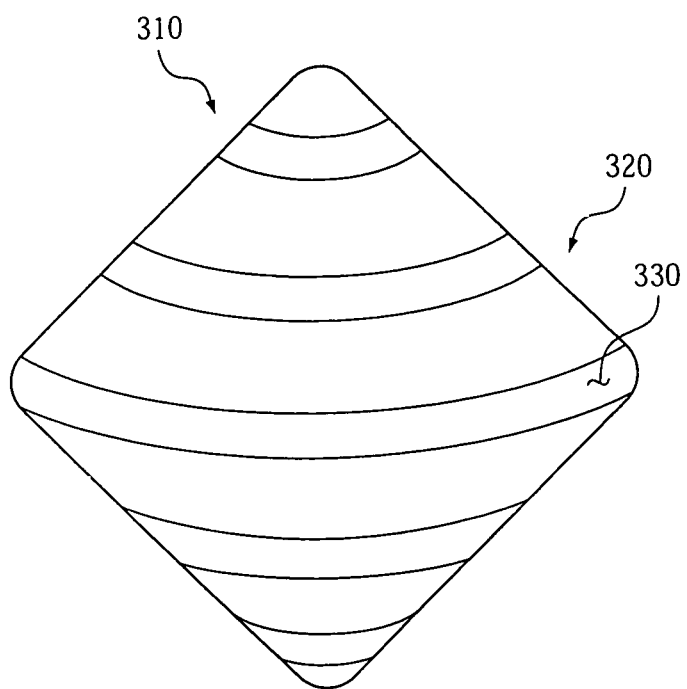
FIG. 5A is a side view of an embodiment of a mandrel.
Figure 5B:
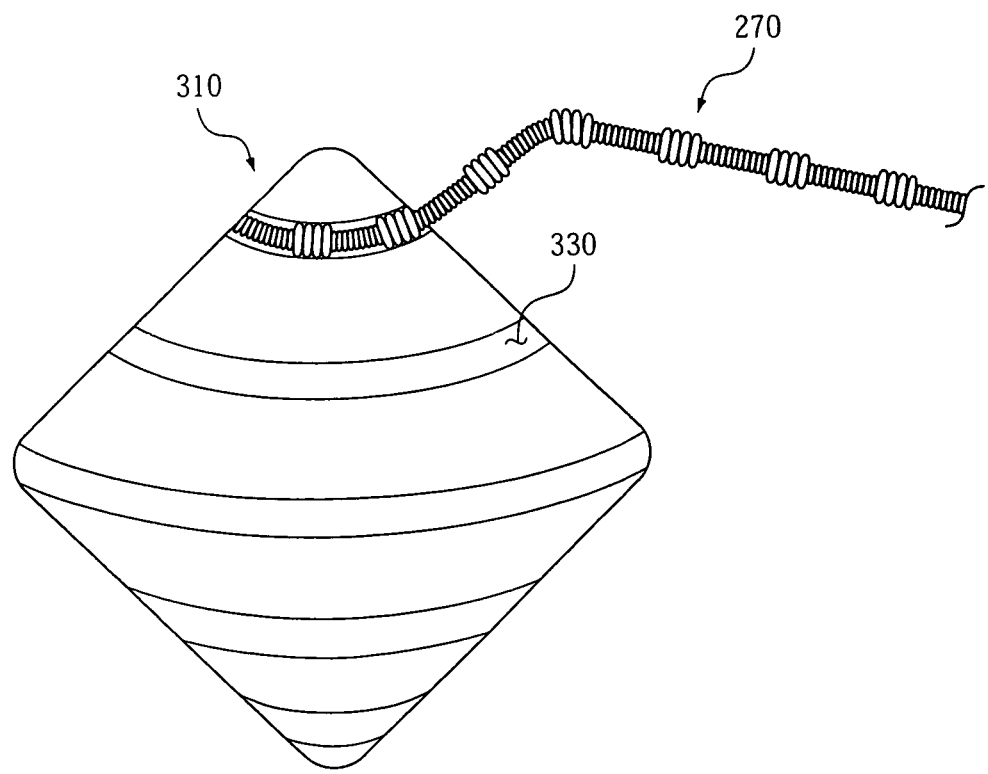
FIGS. 5B and 5C are illustrations of an embodiment of a process for forming an embolic coil using the mandrel of FIG. 5A.
Figure 5C:
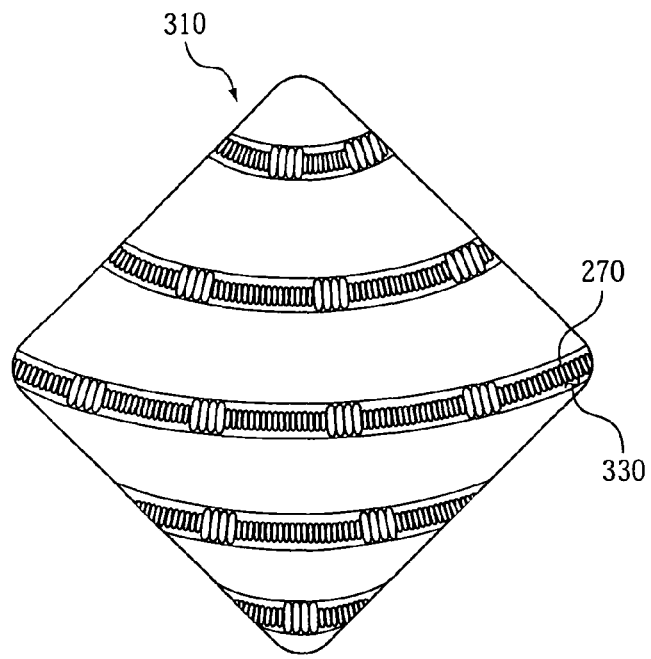

FIG. 4A illustrates a process for forming an embolic coil (e.g., embolic coil 14) in its primary shape, and FIGS. 5A-5C show a process for forming the secondary shape of the embolic coil.

As shown in FIG. 4A, a coil-forming apparatus 200 includes a mandrel 210 held by two rotatable chucks 220 and 230. A spool 240 of wire 250 is disposed above mandrel 210, and is attached to a moving device 260. To form an embolic coil in its primary shape, chucks 220 and 230 are activated so that they rotate in the direction of arrows A2 and A3, thereby rotating mandrel 210. Moving device 260 also is activated, and moves spool 240 in the direction of arrow A1. The rotation of mandrel 210 pulls wire 250 from spool 240 at a predetermined pull-off angle, and causes wire 250 to wrap around mandrel 210. As FIG. 4A shows, the pull-off angle ($\alpha$) is the angle between axis PA1, which is perpendicular to longitudinal axis LA1 of mandrel 210, and the portion 280 of wire 250 between spool 240 and coil 270. In some embodiments, $\alpha$ can be from about one degree to about six degrees (e.g., from about 1.5 degrees to about five degrees, from about 1.5 degrees to about 2.5 degrees, about two degrees). In certain embodiments, a controller (e.g., a programmable logic controller) can be used to maintain the pull-off angle in coil-forming apparatus 200. Because mandrel 210 is rotating as it is pulling wire 250 from spool 240, and because moving device 260 is moving spool 240 in the direction of arrow A1, wire 250 forms a coil 270 in a primary shape around mandrel 210. Coil 270 can be formed, for example, at room temperature (25° C.).

Figure 4B:
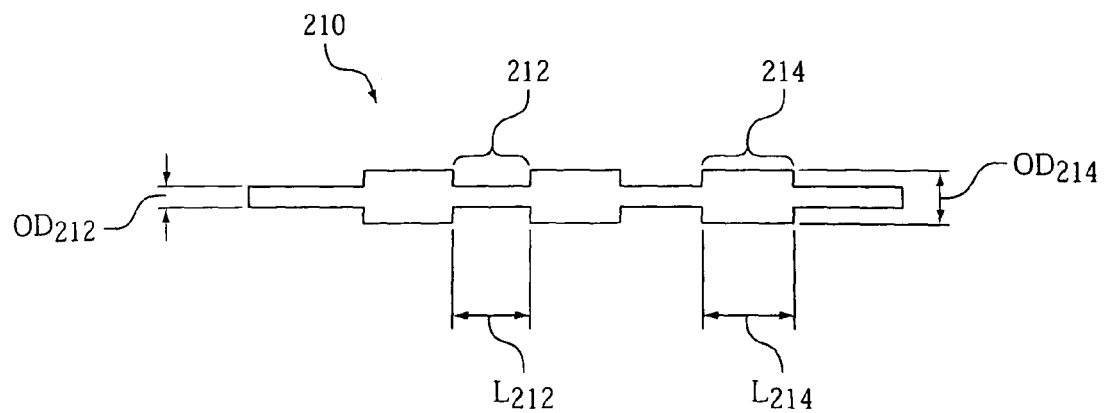
FIG. 4B is a side view of an embodiment of a mandrel used in the process shown in FIG. 4A.

Mandrel 210, also shown in FIG. 4B, has regions 212 of relatively small outer diameter "$OD_{212}$" with a length "$L_{212}$", and regions 214 of relatively large outer diameter "$OD_{214}$" with a length "$L_{214}$". Because coil 270 is formed by wrapping wire 250 around mandrel 210, coil 270 has regions of relatively small outer diameter and regions of relatively large outer diameter that correspond to regions 212 and 214 of mandrel 210.

After coil 270 has been formed, chucks 220 and 230, and moving device 260, are deactivated, and portion 280 of wire 250. Mandrel 210 is then released from chuck 220, and coil 270 is pulled off of mandrel 210. In some embodiments, mandrel 210 can be coated with a lubricious coating (e.g., polytetrafluoroethylene, such as Teflon®) in one or more sections in order to aid in the removal of coil 270 (e.g., to reduce friction and/or snagging). In certain embodiments, the middle section of mandrel 210 is coated, while the ends of mandrel 210 remained uncoated. In some embodiments, mandrel 210 can be hollow, such that after coil 270 has been formed on mandrel 210, pressure can be applied to mandrel 210, causing mandrel 210 to collapse, and thereby making it easier to pull coil 270 off of mandrel 210. Alternatively or additionally, mandrel 210 may be formed of a shape-memory material, such that the size of mandrel 210 can be decreased by cooling mandrel 210. In some such embodiments, mandrel 210 can be cooled prior to removal of coil 270, thereby making it easier to remove coil 270 from mandrel 210. In certain embodiments, mandrel 210 can be formed of an erodible or dissolvable material (e.g., an erodible or dissolvable polymer, metal, or metal alloy). In some such embodiments, after coil 270 has been formed, mandrel 210 can be eroded or dissolved (e.g., by applying an eroding or dissolving agent to mandrel 210), leaving coil 270.

While coil 270 might lose some of its primary shape as it is pulled off of mandrel 210, coil 270 can generally return to its primary shape shortly thereafter, because of memory imparted to coil 270 during formation. In some embodiments, after coil 270 has been removed from mandrel 210, one or both of the ends of coil 270 can be heated and melted to form rounder, more biocompatible (e.g., atraumatic) ends.

In some embodiments, outer diameter "$OD_{212}$" of regions 212 of relatively small outer diameter can be at most about 0.025 inch (e.g., from about 0.012 inch to about 0.013 inch). Alternatively or additionally, length "$L_{212}$" of regions 212 of relatively small outer diameter can be at most about five millimeters.

In certain embodiments, outer diameter "$OD_{214}$" of regions 214 of relatively large outer diameter can be at most about 0.03 inch (e.g., about 0.015 inch). Alternatively or additionally, length "$L_{214}$" of regions 214 of relatively large outer diameter can be at most about 35 centimeters.

In some embodiments, the difference between outer diameter "$OD_{214}$" and outer diameter "$OD_{212}$" can be at most about 0.024 inch (e.g., 0.003 inch). Alternatively or additionally, the ratio of outer diameter "$OD_{214}$" to outer diameter "$OD_{212}$" can be from about 1.05:1 to about 1.5:1 (e.g., from about 1.2:1 to about 1.4:1).

Mandrel 210 can be formed of, for example, a metal or a metal alloy, such as stainless steel. In some embodiments, mandrel 210 can be formed of one or more polymers, such as Teflon® (polytetrafluoroethylene) or Delrin® (polyoxymethylene). As described above, in some embodiments, mandrel 210 can be formed of a shape-memory material. An example of a shape memory material is Nitinol.

Mandrel 210 can be formed, for example, by a wire extrusion process. In certain embodiments, mandrel 210 can be formed by grinding the mandrel material into the shape of mandrel 210 (e.g., using a centerless grind). In some embodiments, mandrel 210 can be formed by using a lathe and/or laser to cut or ablate sections of the mandrel material (e.g., to form regions 212 of relatively small outer diameter). Alternatively or additionally, mandrel 210 can be formed by etching the mandrel material (e.g., using photochemical etching). In certain embodiments, mandrel 210 can be formed by polymeric or metal injection molding.

While mandrel 210 is shown as having relatively sharp edges 211, in some embodiments, mandrel 210 can have relatively rounded edges.

The tension of mandrel 210 as it is held between chucks 220 and 230 preferably is sufficiently high to avoid vibration of mandrel 210 during the winding process, and sufficiently low to avoid stretching of mandrel 210 during the winding process. In some instances, significant stretching of mandrel 210 during the winding process could cause coil 270 to have a smaller primary shape than desired, and/or could make it relatively difficult to remove coil 270 from mandrel 210. In embodiments, the tension of mandrel 210 can be from about 100 grams to about 1,000 grams (e.g., from about 300 grams to about 600 grams, from about 400 grams to about 500 grams). For example, the tension of mandrel 210 can be about 506 grams.

Wire 250 typically can be wound around mandrel 210 at a tension of from about 10 grams to about 100 grams (e.g., from about four grams to about 50 grams, from about six grams to about 40 grams, from about 22 grams to about 32 grams, about 27 grams).

In embodiments, the length of coil 270 in its primary shape and while under tension on mandrel 210 can be from about 10 centimeters to about 250 centimeters (e.g., from about 50 centimeters to about 200 centimeters, from about 130 centimeters to about 170 centimeters, from about 144 centimeters to about 153 centimeters, from about 147 centimeters to about 153 centimeters). For example, the length of coil 270 in its primary shape and while under tension on mandrel 210 can be about 132 centimeters or about 147 centimeters. Coil 270 may recoil to some extent (e.g., by at most about five centimeters) when portion 280 of wire 250 is severed, such that coil 270 will be somewhat smaller once it has been removed from mandrel 210. In embodiments, coil 270 can have a length of from about five centimeters to about 225 centimeters (e.g., from about 25 centimeters to about 170 centimeters, from about 120 centimeters to about 140 centimeters, from about 137 centimeters to about 140 centimeters) after being removed from mandrel 210. After coil 270 has been removed from mandrel 210, coil 270 can be cut into smaller coils.

Once coil 270 has been formed in its primary shape, coil 270 can be further shaped into a secondary shape, as shown in FIGS. 5A-5C.

FIG. 5A shows a mandrel 310 used to form the secondary shape of coil 270. While mandrel 310 is shaped to form a diamond, other types of mandrels can be used to form other secondary shapes. Mandrel 310 is formed of a diamond-shaped block 320 with grooves 330 cut into its surface. As shown in FIGS. 5B and 5C, primary coil 270 is wrapped around mandrel 310, such that coil 270 fills grooves 330, creating the secondary shape. The ends of coil 270 are then attached (e.g., pinned) to mandrel 310, and coil 270 is heat-treated at a temperature of from about 100° F. to about 2000° F. (e.g., from about 500° F. to about 1500° F., from about 1010° F. to about 1125° F.) to impart memory to coil 270. For example, coil 270 can be heat-treated at a temperature of about 1100° F. In some embodiments, the heat treatment of coil 270 can last for a period of from about 10 minutes to about 40 minutes (e.g., about 25 minutes). After being heat-treated, coil 270 is unwrapped from mandrel 310. The removal of coil 270 from mandrel 310 allows coil 270 to reassume its secondary shape. In some embodiments, after coil 270 has been removed from mandrel 310, one or both of the ends of coil 270 can be heated and melted to form rounder, more biocompatible (e.g., atraumatic) ends.

Mandrel 310 can be formed from, for example, a metal such as stainless steel. In some embodiments, mandrel 310 can be formed of a plated metal (e.g., chrome-plated stainless steel).

After coil 270 has been removed from mandrel 310, fibers can be attached to coil 270. In some embodiments, coil 270 is stretched prior to attaching fibers, so that coil 270 is in its extended primary shape, and is then loaded onto a fibering mandrel (e.g., a fibering mandrel from Sematool Mold and Die Co., Santa Clara, Calif.). In some embodiments, fibers can be tied to wire 250 and/or wrapped around wire 250. In certain embodiments, fibers can be snapped in between windings of wire 250 of coil 270. Alternatively or additionally, fibers can be bonded (e.g., adhesive bonded) to wire 250 of coil 270.

While certain embodiments have been described, the invention is not so limited.

As an example, in some embodiments, a coil with a primary shape having regions of relatively small outer diameter and regions of relatively large diameter can be formed by winding a wire around a mandrel with a constant diameter, and varying the tension that is applied to the wire. For example, a tension of from about 10 grams to about 100 grams (e.g., from about six grams to about 50 grams, from about 30 grams to about 40 grams) can be applied to form regions of relatively small outer diameter, and a tension of from about four grams to about 80 grams (e.g., from about four grams to about 40 grams, from about 25 grams to about 29 grams) can be applied to form regions of relatively large outer diameter. In certain embodiments, the difference between the tension used to form regions of relatively small outer diameter and the tension used to form regions of relatively large outer diameter can be from about five grams to about 90 grams (e.g., from about 20 grams to about 80 grams, from about 30 grams to about 50 grams).

As another example, while embodiments have been described in which an embolic coil has two different outer diameters, in certain embodiments, an embolic coil can have more than two (e.g., three, four, five, 10, 15, 20) different outer diameters. For example, an embolic coil can have regions of relatively small outer diameter, regions of intermediate outer diameter, and regions of relatively large outer diameter.

As an additional example, while embodiments have been described in which regions of an embolic coil that have the same outer diameter also have the same length, regions of an embolic coil that have the same outer diameter need not have the same length. For example, an embolic coil can have regions of relatively small outer diameter that have varying lengths. Alternatively or additionally, the embolic coil can have regions of relatively large outer diameter that have varying lengths.

As a further example, in some embodiments, consecutive windings of an embolic coil can have a space between them of at most about 0.01 inch (e.g., at most about 0.005 inch, from about 0.001 inch to about 0.005 inch). The space between consecutive windings in an embolic coil can be used, for example, to accommodate a material that enhances thrombosis, such as fibers that enhance thrombosis.

As another example, while embodiments have been described in which the pitch of an embolic coil is substantially the same in different regions of the embolic coil, in certain embodiments, the pitch of an embolic coil can differ in different regions of the embolic coil. For example, some regions of an embolic coil can have a pitch of 0.003 inch, while other regions of an embolic coil can have a pitch of 0.004 inch. In some embodiments, an embolic coil can have a region of relatively large outer diameter with a relatively small pitch (e.g., about 0.001 inch), and a region of relatively small outer diameter with a relatively large pitch (e.g., about 0.007 inch).

Figure 6:
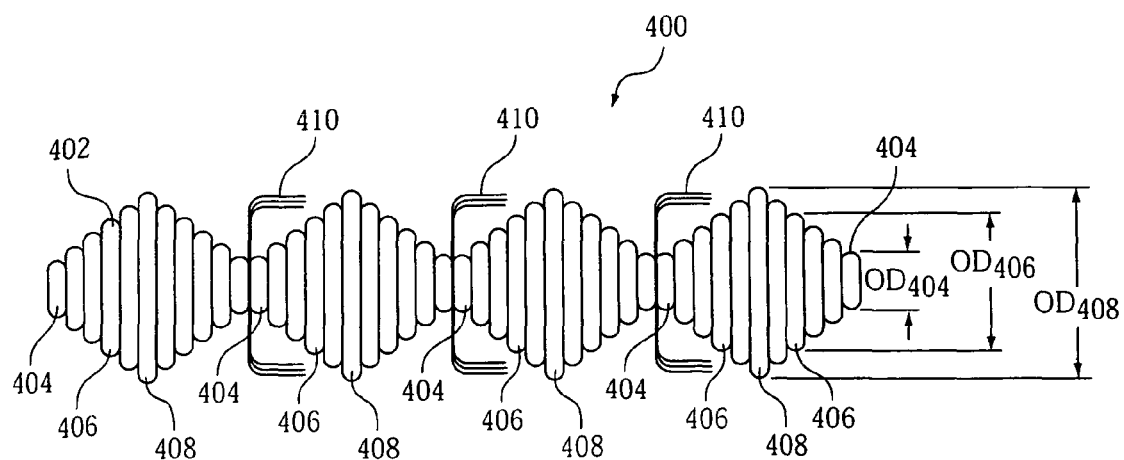
FIG. 6 is a side view of an embodiment of an embolic coil.

As a further example, while an embolic coil with two different outer diameters has been shown, in some embodiments, an embolic coil can have more than two different outer diameters. For example, FIG. 6 shows an embolic coil 400, which is formed out of a wire 402, and which has multiple windings of different outer diameters. Windings 404 have a relatively small outer diameter "$OD_{404}$", windings 406 have an intermediate outer diameter "$OD_{406}$", and windings 408 have a relatively large outer diameter "$OD_{408}$". Fibers 410 are attached to embolic coil 400 in the area of windings 404.

As an additional example, while a pushable embolic coil has been shown, in some embodiments an embolic coil can alternatively or additionally be a detachable embolic coil. For example, the embolic coil can be temporarily attached to a pusher wire. The embolic coil can be, e.g., mechanically detachable and/or chemically detachable. In some embodiments, the embolic coil can be electrolytically detachable. In certain embodiments, the embolic coil can be a Guglielmi Detachable Coil (GDC) or an Interlocking Detachable Coil (IDC). Detachable embolic coils are described, for example, in Twyford, Jr. et al., U.S. Pat. No. 5,304,195, and Guglielmi et al., U.S. Pat. No. 5,895,385, both of which are hereby incorporated by reference.

As a further example, in some embodiments, a saline flush can be used to deliver an embolic coil from a delivery device. In certain embodiments, the saline flush can be used in conjunction with a pusher wire.

As another example, multiple (e.g., two, three, four) embolic coils can be delivered using one delivery device.

As an additional example, in some embodiments, a treatment site can be occluded by using coils in conjunction with other occlusive devices. For example, coils can be used with embolic particles such as those described in Buiser et al., U.S. Published Patent Application No. 2003/0185896 A1, and in U.S. Patent Application Publication No. US 2004/0096662 A1, published on May 20, 2004, both of which are hereby incorporated by reference. In some embodiments, coils can be used in conjunction with one or more embolic gels. Embolic gels are described, for example, in U.S. patent application Ser. No. 10/927,868, filed on Aug. 27, 2004, and entitled "Embolization", which is hereby incorporated by reference.

Other embodiments are in the claims.

What is claimed is:

1. An embolic coil including a wire having a primary shape when extended in a lumen of a deployment device, the primary shape with a plurality of first regions each having a first outer diameter, each of the first outer diameters being substantially the same, and a plurality of second regions each having a second outer diameter that is smaller than the first outer diameter, each of the second outer diameters being substantially the same,
   wherein:
      the embolic coil is configured to fit within a lumen of a subject;
      at least one of the plurality of second regions is located between two of the plurality of first regions; and
      at least one of the first regions comprises multiple windings with adjacent windings being flush with each other.

2. The embolic coil of claim 1, wherein the first outer diameter is at most about 0.03 inch.

3. The embolic coil of claim 1, wherein the second outer diameter is at most about 0.025 inch.

4. The embolic coil of claim 1, wherein a difference between the first outer diameter and the second outer diameter is at most about 0.024 inch.

5. The embolic coil of claim 1, wherein a ratio of the first outer diameter to the second outer diameter is at least about 1.05:1.

6. The embolic coil of claim 1, further comprising at least one fiber attached to the wire.

7. The embolic coil of claim 6, wherein the at least one fiber is attached to a region of the wire having the second outer diameter.

8. The embolic coil of claim 6, wherein the at least one fiber comprises polyethylene terephthalate or nylon.

9. The embolic coil of claim 6, wherein the at least one fiber has a length of from about 0.5 millimeter to about five millimeters.

10. The embolic coil of claim 1, wherein the embolic coil has an effective column strength of from 0.005 pound to about 0.05 pound.

11. The embolic coil of claim 1, wherein the wire has a diameter of from 0.001 inch to 0.005 inch.

12. The embolic coil of claim 1, wherein the wire comprises a metal.

13. The embolic coil of claim 1, wherein the wire has a secondary shape that is a J, a diamond, a vortex, or a spiral.

14. The embolic coil of claim 1, wherein the plurality of first regions and the plurality of second regions are arranged in an alternating sequence.

15. The embolic coil of claim 1, wherein the embolic coil has a pitch that is at most 0.003 inch.

16. The embolic coil of claim 1, wherein the embolic coil has a pitch of at most 0.01 inch.

17. The embolic coil of claim 16, wherein the plurality of first regions and the plurality of second regions are arranged in an alternating sequence.

18. The embolic coil of claim 17, the wire has a secondary shape that is a J.

19. The embolic coil of claim 17, the wire has a secondary shape that is a diamond, a vortex, or a spiral.

20. The embolic coil of claim 17, wherein the wire has a diameter of from 0.001 inch to 0.005 inch.

21. The embolic coil of claim 17, wherein the plurality of first regions and the plurality of second regions are arranged in an alternating sequence.

22. The embolic coil of claim 17, wherein the first outer diameter is at most about 0.03 inch.

23. The embolic coil of claim 22, wherein the second outer diameter is at most about 0.025 inch.

24. The embolic coil of claim 17, wherein a difference between the first outer diameter and the second outer diameter is at most about 0.024 inch.

25. The embolic coil of claim 17, wherein a ratio of the first outer diameter to the second outer diameter is at least about 1.05:1.

26. The embolic coil of claim 1, wherein the at least one of the second regions comprises multiple windings with adjacent windings being flush with each other.

27. A medical device, comprising:
a tubular body defining a lumen; and
at least one embolic coil disposed within the lumen, the at least one embolic coil including a wire having a primary shape when extended in the lumen, the primary shape with a plurality of first regions each having a first outer diameter, each of the first outer diameters being substantially the same, and a plurality of second regions each having a second outer diameter that is smaller than the first outer diameter, each of the second outer diameters being substantially the same;
wherein at least one of the plurality of second regions is located between two of the plurality of first regions, and at least one of the first regions comprises multiple windings with adjacent windings being flush with each other.

28. The medical device of claim 27, wherein the at least one embolic coil comprises multiple embolic coils.

29. The medical device of claim 27, further comprising a pusher wire.

30. The medical device of claim 29, wherein the pusher wire is disposed within the lumen of the tubular body and attached to the embolic coil.

31. The medical device of claim 27, wherein the tubular body comprises a catheter.

* * * * *